United States Patent [19]

Fleming

[11] Patent Number: 4,966,319
[45] Date of Patent: Oct. 30, 1990

[54] ORTHODONTAL DEVICE CARRYING CASE WITH NECK STRAP

[75] Inventor: Jim Fleming, Kleinburg, Canada

[73] Assignee: Jim Fleming Communications, Kleinburg, Canada

[21] Appl. No.: 430,592

[22] Filed: Nov. 2, 1989

[51] Int. Cl.⁵ .................... A45C 13/30; A61C 19/02
[52] U.S. Cl. ...................... 224/207; 206/83; 206/459; 220/339; 224/205; D9/420; D9/424
[58] Field of Search ............. 206/83, 37, 38; 220/338, 339, 94 R, 4 B; 224/202, 205, 207; D9/420, 424, 425, 426, 423; D24/10, 16; 229/2.5 R

[56] References Cited

U.S. PATENT DOCUMENTS

| | | | |
|---|---|---|---|
| D. 257,790 | 1/1981 | Kesling | D9/424 X |
| 1,340,957 | 5/1920 | Hummel | 224/207 |
| 1,712,680 | 5/1929 | Svensson | 206/37 X |
| 2,196,566 | 4/1940 | Sabahis | 206/83 |
| 2,262,360 | 11/1941 | Gottlieb | 206/806 X |
| 2,375,645 | 5/1945 | Gordon | 206/83 |
| 2,444,294 | 6/1948 | Jones | 206/83 |
| 2,777,492 | 1/1957 | Kikuchi | 220/339 X |
| 2,852,054 | 9/1958 | Motley | 220/339 X |
| 3,292,252 | 12/1966 | Reading | 220/4 B X |
| 3,392,820 | 7/1968 | Azim | 220/338 X |
| 3,402,808 | 9/1968 | Yannuzzi | 206/37 X |
| 3,499,525 | 3/1970 | Kanter | 220/339 X |
| 3,567,085 | 3/1971 | Flores | 224/202 |
| 3,734,336 | 5/1973 | Rankor et al. | 220/94 R X |
| 3,750,869 | 8/1973 | Kartiganer | 220/4 B X |
| 3,889,805 | 6/1975 | Korten | 220/4 B X |
| 4,013,214 | 3/1977 | Hansen et al. | 220/4 B |
| 4,096,986 | 6/1978 | Florian | 220/4 B X |
| 4,650,073 | 3/1987 | Young | 224/205 X |
| 4,697,700 | 10/1987 | Weissman | 206/83 |

Primary Examiner—Bryon P. Gehman

[57] ABSTRACT

The present invention provides a carrying case for an orthodontal device. The carrying case comprises a plastic body formed by first and second body portions hingedly connected to one another and including a releasable closure to open and close the first and second body portions which, when closed with one another, have a combined depth for storage of the orthodontal device interiorly of the carrying case. The carrying case further includes an external specified indicia receiving region for receiving identifying information such as for example the name of the owner of the carrying case and the name of the orthodontist which appears to the outside of the carrying case.

2 Claims, 2 Drawing Sheets

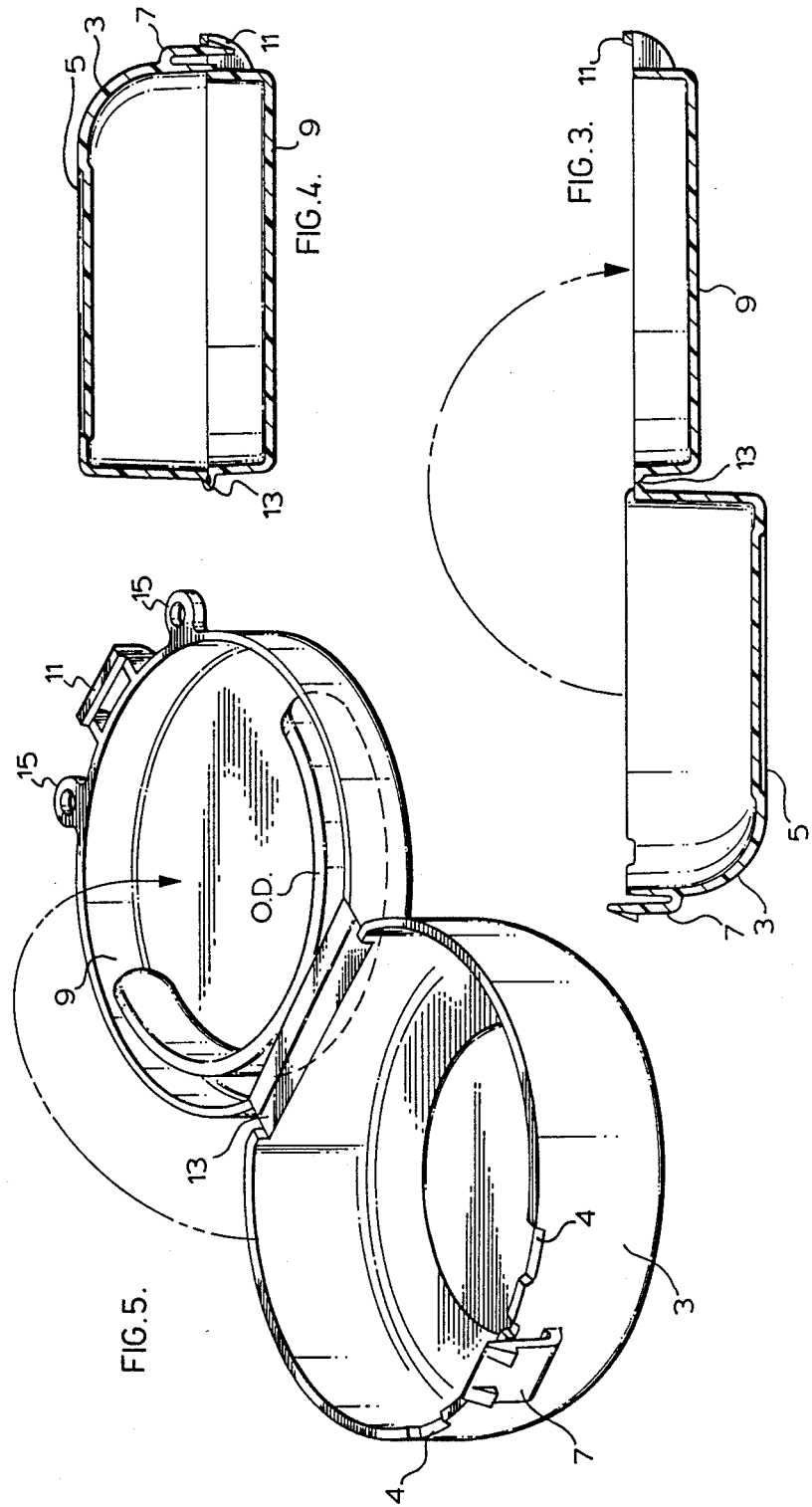

ORTHODONTAL DEVICE CARRYING CASE WITH NECK STRAP

FIELD OF THE INVENTION

The present invention provides a carrying case, specifically for receiving an orthodontal device such as lip appliances or "bumpers" as they are commonly known as well as removable braces or temporary bridges, etc.

BACKGROUND OF THE INVENTION

Many people require the use of an orthodontal device which is removed for eating or during specific physical activities. Generally speaking, most people do not have anything in the way of a carrying case for these orthodontal devices which are therefore subject to loss and/or non-hygenic conditions. Furthermore, once the device has been removed, one may often forget to return it to ones mouth after the eating or physical activity has been completed.

SUMMARY OF THE PRESENT INVENTION

The present invention provides a carrying case specifically for an orthodontal device. The carrying case may, for example, be worn around ones neck and be of a highly visible colour, etc. so that it is both appealing and attracts attention so that one does not forget to return the orthodontal device to ones mouth after it has been removed.

In particular, the orthodontal device carrying case of the present invention comprises a plastic body formed by first and second body portions hingedly connected to one another and includes releasable closure means for releasably closing the first and second body portions with one another which then have a combined depth for storage of the orthodontal device interiorly of the carrying case.

In addition, the carrying case includes an externally provided indicia receiving region for receiving identifying information regarding the carrying case. This identifying information can be in the form of a label and the like bearing the name of the owner of the case, the orthodontist, etc.

BRIEF DESCRIPTION OF THE DRAWINGS

The above as well as other advantages and features of the present invention will be described in greater detail according to the preferred embodiments of the present invention in which;

FIGS. 3 and 4 are sectional views through the orthodontal device carrying case of FIG. 2 in the open and the closed positions respectively;

FIG. 5 is a further perspective view of the orthodontal device carrying case of FIG. 2 in the open position.

DETAILED DESCRIPTION ACCORDING TO THE PREFERRED EMBODIMENTS OF THE PRESENT INVENTION

Figure 1:
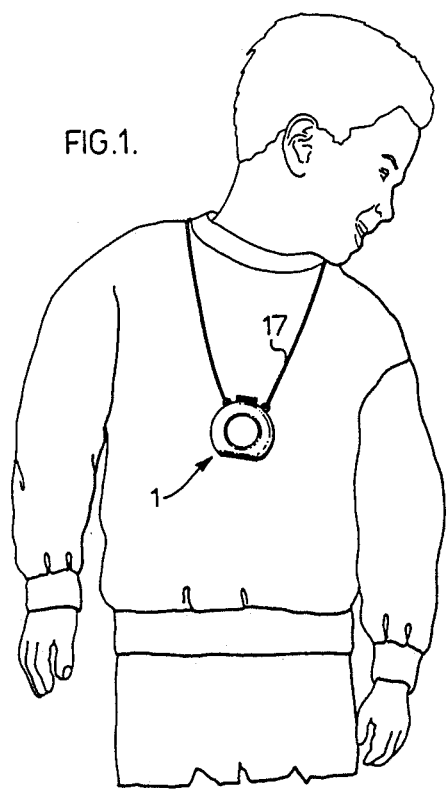
FIG. 1 is a perspective view of a child wearing an orthodontal device carrying case made in accordance with a preferred embodiment of the present invention.
Figure 2:
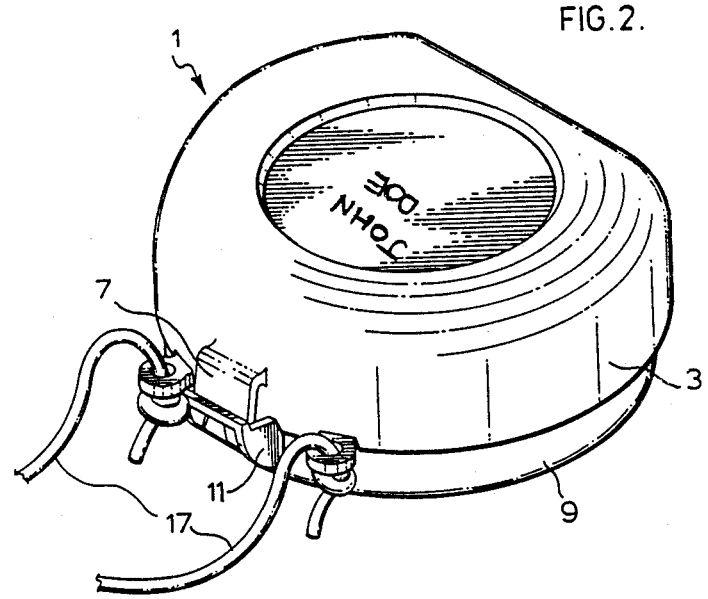
FIG. 2 is an enlarged perspective view of the orthodontal device carrying case of FIG 1.

FIG. 1 shows a young child wearing an orthodontal device carrying case generally indicated at 1. This case is supported about the child's neck by means of a strap or string 17, which is secured to the case as best seen in FIG. 2 of the drawings.

The carrying case is formed by first and second or top and bottom body portions 3 and 9 respectively. These two body portions are hingedly connected to one another by means of a "living" hinge 13. The entire construction including both body portions and the hinge are preferably formed from a single piece of extrusion molded plastic keeping the cost of the case to a minimum while maintaining accurate specifications for the case. The particular plastic used will be one which is durable while being shock and impact resistant.

In the preferred embodiment, the case is about 3.75" in diameter and has an interior depth in a closed position of about 1.25". These dimensions are specifically designed to receive an orthordontal device OD as best seen in FIG. 5 of the drawings. This orthodontal device may be in the form of a lip bumper, removable braces, temporary bridges, etc.

The case is provided with releasable closure means in the form of a snap closure comprising interlock components 7 and 11 provided on body portions 3 and 9 respectively. Again, these interlock portions are formed from the single piece of molded plastic and are resilient to the extent that they quickly and easily interlock with one another and do not fatigue even after many uses of the snap closure.

The carrying case further includes integrally molded eyelets 15, which in the embodiment shown are provided on body portion 9. They could equally as well be provided on body portion 3. Note that body portion 3 is provided with cutout regions 4 which cooperate to fit with the eyelets 15 with the carrying case in its closed position.

As will be best seen in FIG. 4, the carrying case is extremely well sealed when in the closed position and of particular interest is the hinge area where the use of a living hinge, i.e. a hinge integral with the remainder of the structure does not have any open areas and therefore does not allow any contaminants to enter the carrying case.

The carrying case is extremely light in weight with the neck straps 17 being fitted through eyelets 15 to allow wearing of the carrying case around ones neck and the like. In a very simple arrangement, the neck strap may comprise a woven synthetic cord knotted at each end to trap the cord at the eyelets.

A further feature of the present invention is the provision of an externally depressed region 5 provided on body portion 3. Again, it is to be appreciated that depressed region 5 could equally as well be provided on body portion 9.

Depressed region 5 comprises an indicia receiving region, primarily designed for receiving a stick on label or the like which will in turn bear identifying information such as the owner of the carrying case, the orthodontist responsible for the device, etc. As a result of the inward or downward depressing of region 5, it is out of the plane of the remainder of the case and therefore, the identifying information on the label or the like is much less subject to wear than is the remainder of the case so that the identifying information is not likely to be inadvertently worn off of the label or the like.

As a result of the plastic construction of the carrying case, it is easily washed and once again, the particular plastic material selected is one which is resistant to high water temperatures and the like so that the carrying case can, for example, be placed directly in the dishwasher. This again adds to the hygenic aspects of the carrying case.

In the preferred embodiment, the carrying case is brightly coloured to attract the attention of the wearer so that he or she not only wants to wear the carrying case, but in addition, will not forget to use the carrying case for its intended purposes.

Although various preferred embodiments of the invention have been described in detail, it will be appreciated that variations may be made without departing from the spirit of the invention or the scope of the appended claims.

The embodiments of the invention in which an exclusive property or privilege is claimed are defined as follows:

1. An orthodontal device carrying case to be hung downwardly from one's neck, said case comprising a plastic body formed by a first body portion having an interior region for receiving the orthodontal device and a second body portion for closing with said first body portion and covering the orthodontal device, a hinge between said first and second body portions at one end of said case, and a releaseable closure at the other end of said device, eyelets for receiving a neck strap to hang said case, said eyelets being provided on said first body portion in balanced positions to either side of said releaseable closure substantially diametrically opposite said hinge, said second body portion being provided with an external indicia receiving depression with identifying information regarding said carrying case.

2. An orthodontal device and carrying case combination, said case comprising a plastic body formed by a first body portion in which said orthodontal device is located and a second body portion for closing with said first body portion and covering said orthodontal device, a hinge at one end of said body between said body portions and a releaseable snap closure at the other end of said body, eyelets on said first body portion in balanced positions to either side of said releaseable snap closure, and a neck strap fitted through said eyelets, said eyelets being located substantially diametrically opposite said hinge, said second body portion including recesses in which said eyelets are located when said first and second body portions are closed with one another and said second body portion further being provided with an external indicia receiving depression with identifying information regarding said carrying case provided in said depression.

* * * * *